(12) United States Patent
Penman et al.

(10) Patent No.: US 9,671,354 B2
(45) Date of Patent: Jun. 6, 2017

(54) METHOD OF ELECTRON BEAM DIFFRACTION ANALYSIS

(71) Applicant: Oxford Instruments Nanotechnology Tools Limited, Oxon (GB)

(72) Inventors: Charles Penman, Bucks (GB); Niels-Henrik Schmidt, Bucks (GB); Knud Thomsen, Bucks (GB)

(73) Assignee: Oxford Instruments Nanotechnology Tools Limited (GB)

( * ) Notice: Subject to any disclaimer, the term of this patent is extended or adjusted under 35 U.S.C. 154(b) by 0 days.

(21) Appl. No.: 14/768,135

(22) PCT Filed: Feb. 14, 2014

(86) PCT No.: PCT/GB2014/050444
§ 371 (c)(1),
(2) Date: Aug. 14, 2015

(87) PCT Pub. No.: WO2014/012595
PCT Pub. Date: Aug. 21, 2014

(65) Prior Publication Data
US 2015/0369760 A1    Dec. 24, 2015

(30) Foreign Application Priority Data
Feb. 15, 2013  (GB) .................................. 1302694.3

(51) Int. Cl.
*G01N 23/203* (2006.01)
*H01J 37/26* (2006.01)

(52) U.S. Cl.
CPC .......... *G01N 23/203* (2013.01); *H01J 37/261* (2013.01)

(58) Field of Classification Search
USPC ....................................................... 250/307
See application file for complete search history.

(56) References Cited

U.S. PATENT DOCUMENTS 5,063,604 A * 11/1991 Weiman ............... G06K 9/4633
382/170
6,326,619 B1 * 12/2001 Michael .............. H01J 37/2955
250/307

(Continued)

OTHER PUBLICATIONS

J. A. Small, et al., "Phase Identification of Individual Crystalline Particles by Electron Backscatter Diffraction", Journal of Microscopy, vol. 201. Pt. 1, Jan. 2001, pp. 59-69.

(Continued)

*Primary Examiner* — Phillip A Johnston
(74) *Attorney, Agent, or Firm* — Blank Rome LLP

(57) ABSTRACT

A method is provided for analysing electron backscatter diffraction data generated from a sample material. An image data set representative of an image of electron backscatter diffraction bands is obtained from the sample material. A set of estimated first diffraction parameters is then generated, these defining individual electron backscatter diffraction bands in the image data set. A candidate phase is then selected together with a respective orientation for the material, based upon the generated set of estimated parameters thereby identifying diffraction bands in the image data set. Second diffraction parameters of the identified diffraction bands are simulated for the candidate phase according to the respective orientation. These second diffraction parameters are then adjusted for the identified simulated bands so as to fit the simulated bands to the bands in the image data. A fitted orientation for the candidate phase is then calculated together with a corresponding fitting parameter defining the quality of fit. The second diffraction parameters are rho and phi angles, each of which is modulated independently during the said adjusting of a fit to a single band.

18 Claims, 8 Drawing Sheets

(56) References Cited

U.S. PATENT DOCUMENTS

2004/0011958 A1 1/2004 Wright et al.
2010/0158392 A1* 6/2010 Adams .................. B82Y 30/00
382/218

OTHER PUBLICATIONS

D. Dingley, "Progressive steps in the Development of Electron Backscatter Diffraction and Orientation Imaging Microscopy", Journal of Microscopy, vol. 213, Pt. 3, Mar. 2004, pp. 214-224.

* cited by examiner

METHOD OF ELECTRON BEAM DIFFRACTION ANALYSIS

RELATED APPLICATIONS

This application is a national phase application of PCT/GB2014/050444, filed Feb. 14, 2014, which claims priority to Great Britain Patent Application No. 1302694.3, filed Feb. 15, 2013, the entire contents of which are incorporated herein by reference.

FIELD OF THE INVENTION

A method is provided for electron beam diffraction analysis in which electron backscatter diffraction (EBSD) data generated from a sample material is analysed.

BACKGROUND TO THE INVENTION

Electron backscatter diffraction analysis is a well established technique of materials analysis. It is a crystallographic method used to identify materials, phases, grain orientation and texture on the micro-scale, as well as to map strain and characterise defects, and relies on analysis of electron "Kikuchi" patterns obtained using a focused electron beam in a scanning electron microscope, either in a backscattered or a transmission geometry. A typical Kikuchi pattern is shown in FIG. 1.

Various numerical methods have been devised to obtain such information from Kikuchi diffraction patterns of crystals, these all requiring a compromise between computational load and accuracy of measurement. Commonly, analysis methods for Kikuchi patterns rely on the "2D Hough transform" approach, where an area of interest is selected on the Kikuchi pattern and a 2D Hough transform is applied to highlight and locate line structure in the pattern corresponding to the Kikuchi bands, as published by N C Krieger Lassen, "Automated Determination of Crystal Orientations from Electron Backscattering Patterns", Ph.D Thesis 1994, Technical University of Denmark, DK-2800 Lyngby. Kikuchi bands are revealed as local peaks in the resulting Hough space and their corresponding maxima are found automatically, thus detecting the position and orientation of Kikuchi bands and their corresponding diffraction planes. These detected planes are queried against a database of known phases, and the orientation of the now identified crystal phase is calculated with respect to the overall specimen geometry. Precision and accuracy of this process are limited primarily by the precision of identifying and locating the Kikuchi bands, which in turn is limited by the Hough transform. FIG. 2 shows how pairs of Kikuchi lines are described in the polar parameters (rho, phi) for the Hough transform. The distance L in FIG. 2 indicates the width of the band. The precision in the orientation measurement is, in a first instance, improved by increasing the resolution of the Hough transform and the resulting Hough space, however this results in a much increased computational effort and is undesirable. Further, the Hough transform makes the assumption that the bands are straight segments with constant separation L, whereas Kikuchi bands are hyperbolic, and therefore a systematic error is introduced by the conventional Hough transform, which cannot be overcome through increased Hough space resolution. These problems of precision and accuracy have been addressed by a number of investigators.

A first method, published by C Maurice and R Fortunier, "A 3D Hough transform for indexing EBSD and Kossel patterns", Journal of Microscopy, vol. 230, 2008, pp. 520-529, consists of extending the Hough transform such that it identifies hyperbolic curves rather than straight lines, where a new hyperbola variable is used in addition to the conventional distance and angle variables. This "Sin theta" variable, which is proportional to the width of the band, L, represents the Bragg reflection condition, However, without knowledge of the crystalline structure, this hyperbola parameter is unknown at the time of the Hough transform and therefore must be varied over a specified range to explore all possible Bragg angles that govern the separation of the two hyperbolic edges for the band. The result of this extended Hough transform is a three-dimensional space (illustrated in FIG. 3), where the third dimension is given by the hyperbola variable, and a given point in this space represents a unique conic section as opposed to just a straight line as with the conventional 2D Hough transform. As with the conventional method, the corresponding local peaks in this three-dimensional space need to be detected to identify the diffraction parameters. Whilst this modified Hough transform removes the systematic error of the conventional Hough transform, it is computationally expensive due to the large three dimensional calculation space, and is therefore slow.

A second method, was reported by J A Small and J R Michael, "Phase identification of individual crystalline particles by electron backscatter diffraction", Journal of Microscopy, 201(1), 2001, pp. 59-69, and consists of using the band information provided by the 2D Hough method to find the closest match in a database of phases. Using data for the best candidate phase the expected bands are simulated using the correct hyperbolic shape and compared with the measured pattern to provide a visual confirmation that the correct phase has been identified.

In a third method, D J Dingley and S I Wright, "Phase Identification Through Symmetry Determination in EBSD Patterns" book chapter in "Electron Backscatter Diffraction in Materials Science Second Edition", Springer 2009, ISBN 978-0-387-88135-5, pages 99-103, use additional symmetry measures to find potential candidate phases. Having found a candidate that would generate a pattern with the observed symmetry, they simulate the pattern and vary the lattice parameter in small increments until there is good visual correspondence with some of the bands in the measured pattern.

The second and third methods involve user interaction (such as visual observation) to validate an accurate simulation against the observed pattern and the first method is computationally expensive.

There is a general and long standing need for a practical analysis method with much improved precision and reduced computational load, that does not require manual intervention and this is the object of the present invention.

SUMMARY OF THE INVENTION

In accordance with the present invention we provide a method for analysing electron backscatter diffraction data generated from a sample material, comprising:
a) obtaining an image data set representative of an image of electron backscatter diffraction bands from the sample material;
b) generating a set of estimated first diffraction parameters defining individual electron backscatter diffraction bands in the image data set;

c) selecting a candidate phase and a set of plane indices consistent with a set of calculated plane normals for at least a subset of the defined diffraction bands;
d) simulating second diffraction parameters of identified diffraction bands for the candidate phase;
e) adjusting the second diffraction parameters for the identified simulated bands so as to fit the simulated bands to the bands in the image data; and,
f) calculating a fitted orientation for the candidate phase together with a corresponding fitting parameter defining the quality of fit,
wherein the second diffraction parameters are rho and phi angles, each of which is modulated independently during the said adjusting of a fit to a single band.

Thus an improved method is provided for analysis of diffraction patterns. The method may be thought of as follows. An initial part of the method applies the established method of analysis on the original or a reduced resolution copy of the experimental image data, which identifies straight lines in the diffraction pattern using the Hough transform, and employs a crystallographic database to find one or more candidate solutions for phase and plane indices. The method then uses a refinement procedure that uses some properties of a candidate solution to more accurately simulate one or more Kikuchi bands and adjusts parameters that influence the shape and position of these bands to achieve a better fit. The fitting is performed upon selected individual bands in the imaging space. Additional parameters for the candidate solution are calculated in concordance with the fitted Kikuchi bands and a measure of goodness of fit is obtained by comparing predictions from the refined specimen model with measurements from the fitted Kikuchi bands. This measure can be used as a measure of accuracy or be used to select between alternative candidate solutions and associated specimen models.

Whereas the initial analysis of the pattern does not use any crystallographic information, may use a reduced resolution version of the original data to speed up computation and gives a result with limited accuracy, the refinement procedure uses additional crystallographic information about the candidate phase of the specimen to generate an accurate simulation for such a phase that can be compared with the original high resolution pattern, and produce a result with much greater accuracy. Furthermore, because the refinement procedure only uses selected bands in the image, computation effort is not spent evaluating pixels that do not contain relevant diffraction information. Thus, high accuracy is obtained with an efficient computational approach.

In other words, this invention provides an analysis method that uses a refinement algorithm informed by additional knowledge of physical properties of the assumed specimen phase under observation, and thus improves efficiency of calculation as well as accuracy of crystallographic measurements.

The benefits of the invention are significant. These include higher angular resolution of orientation measurements, increased robustness of phase identification, and direct measurements of plastic deformation. Each of these benefits is much sought after in the field of EBSD analysis.

Turning now to some of the specific steps within the method, typically the second diffraction parameters which are simulated in step (d) are rho and phi parameters, each of which is modulated independently during the said adjusting for each individual band. Further advantage may be provided by the use of the Bragg angle as an additional parameter for modulation since this affects the width of the band L. In one approach the second diffraction parameters are modified iteratively in order to maximise the sum of slopes in image data values across the simulated band edges. For example the slope may be measured in the rho direction and defined positive if the change in image value decreases away from the band centre. This provides a fast and accurate fit to the individual bands in the image. As will be understood the reverse slope polarity would apply in an image having reversed contrast.

Typically the fitting parameter in step (f) is based upon a correlation measure. The fitting parameter may take the form of a mean angular deviation between the adjusted simulated band angles and predicted band angles for the candidate phase in the optimum orientation. The mean angular deviation is typically the mean absolute difference, or could be the mean square difference.

Alternatively, the second diffraction parameters may define the crystal orientation, and can include the "d-spacings" as well. In either case the second diffraction parameters may be modified iteratively in accordance with a correlation measure representing the correlation between all the chosen bands in the image data set and simulated bands in simulated images. The correlation measure may be represented by a mathematical combination of slopes in image data values across the simulated band edges, the slope being measured in the rho direction and defined positive if the change in image value decreases away from the band centre. In this case the fitting parameter in step (f) is based upon the same correlation measure.

The size of the image dataset may have a significant influence on the computational resources needed to perform the method. In the case of the initial image data set, we have found that the size of the image data set may be advantageously reduced whilst maintaining the quality of the process results as a whole. Thus, prior to step (a) the image data set used in the method may be produced by processing an initial image data set so as to reduce the size of the image data set in comparison with the initial image data set.

The first diffraction parameters in step (b) may be obtained by the steps of:
(i) applying a Hough transform to the image data set forming transformed data in Hough space, and
(ii) detecting Kikuchi bands in the Hough space.

Thereafter, step (c) preferably includes interpreting the detected Kikuchi bands to determine plane normals and comparing these with crystallographic data so as to index at least a subset of the bands.

In many practical situations, the availability of computational resources (such as computational power) is limited. This in turn places limitations upon the overall speed of the process or may require preselection of candidate materials so as to reduce the number of calculations for example. Such limitations are generally undesirable. However, one great advantage of the inventive method is that, in step (d), it is possible to restrict the number of bands simulated to those most likely to improve the solution. This makes efficient use of the simulation since only a subset of detected bands are used. For example, the first Hough routine in (b) will try to find well-defined bands that give more than a threshold intensity in the Hough transform. With knowledge of the camera geometry, the interplanar angles between each pair of bands can be calculated giving a large set of interplanar angles. A database of candidate materials contains a list of interplanar angles for all planes likely to contribute to a pattern and the measured set is compared with the set for each material to find a set of indices for the bands that is consistent with the crystal structure for the material. It is likely that some of the measured bands will not fit, but the bands that contribute to likely interplanar angles can now be identified with particular crystal planes and these bands can thus be "indexed". The refinement method is only applied to those bands that have been successfully indexed and this is typically 6 to 12 bands. The number of bands simulated may be made equal to the number of bands for which estimated diffraction parameters are generated in step (b) and where the band has been successfully indexed by matching of interplanar angles with those for a candidate phase. In order to increase the accuracy of the method, the effect of the adjustment in step (e) may be calculated at a number of separated locations along the bands.

In addition to the core method described in accordance with steps (a) to (f), it is desirable to make these steps central to a method for a more "end to end" process for identifying materials which is attractive to a practical user. Ideally such a method may be unsupervised so as to enable users who are not skilled in EBSD to perform materials analysis using the method. Hence, the method may further comprise, selecting a plurality of candidate phases and indices in accordance with step (c), performing steps (d), (e) and (f) for each candidate phase and selecting a resultant phase and associated fitted orientation based upon the fitting parameter for each candidate phase.

As an additional step which may assist with a user of a system implementing the method an image of the bands of the image data set may be overlaid with the simulated bands so as to provide a visual representation of the correlation.

Furthermore, particularly when implemented in EBSD analysis equipment the method may be repeated for a number of scan points on the sample so as to produce a map of crystallographic properties.

The present method is primarily computer-implemented in that the steps may be executed upon a computer system and include the receipt, processing and generation of data relevant to the EBSD analysis. It is particularly desirable that the method, after setting up suitable criteria for decision making in the algorithm, can run unsupervised in order to produce a map of crystallographic properties. The unsupervised aspect is also an important differentiator compared with known prior methods that present a solution visually and depend on interaction with the user to refine the solution. The novel use of a metric to show the goodness of fit of the bands is an important enabler of the unsupervised approach and automation.

BRIEF DESCRIPTION OF THE DRAWINGS

We now described a method of electron beam diffraction analysis with reference to the accompanying drawings, in which.

DESCRIPTION OF EXAMPLES

The example we now describe is a particular implementation to increase precision in orientation mapping and phase identification, and does not preclude other embodiments that may be used to calculate plastic deformation in the crystal, or to map out sub-grain structures for example.

The method may be performed using largely conventional EBSD analysis apparatus, this of course including a chamber for containing a sample to be analysed, an electron beam source and a detector for obtaining EBSD data. The apparatus should also contain or be in communication with a computer system for performing the analysis of the data. Such a computer system may contain a database of materials data allowing simulations of EBSD data to be made and specific known materials to be identified. As will be understood such a computer system may include distributed devices such as a remote database of materials accessible over a network such as the Internet.

Figure 4:
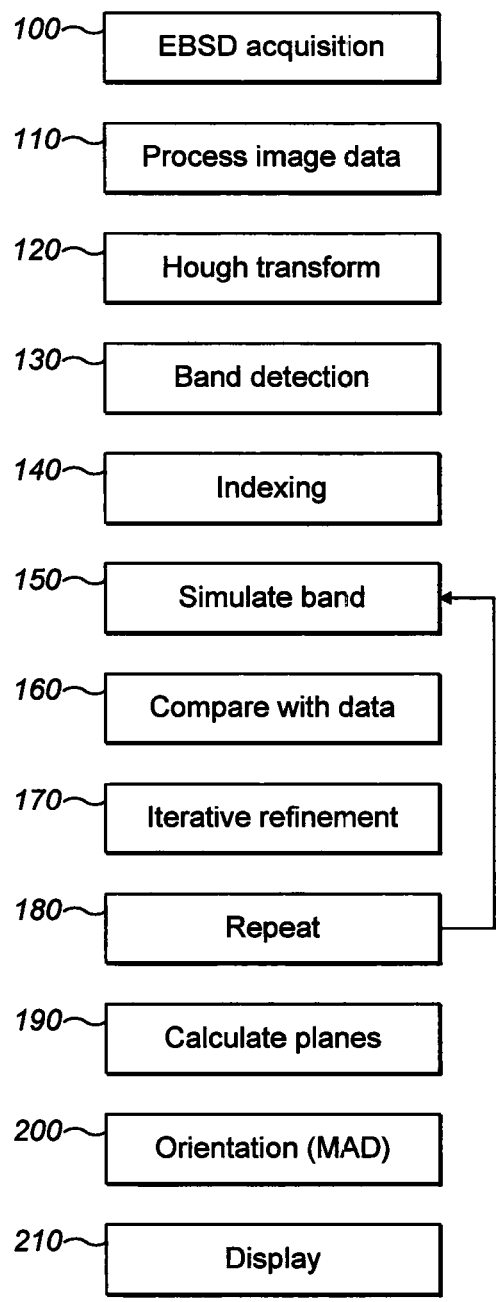
FIG. 4 is a flow diagram of an example method.

We now refer to FIG. 4 which is a flow diagram of the example method.

In a first step 100 in FIG. 4 a user places a sample to be analysed within EBSD apparatus of the type discussed above. The user then operates the apparatus so as to obtain data representing an appropriate EBSD image for analysis, such an image including Kikuchi bands.

At step 110, a data processing operation is performed. In the present case one goal of this process is so as to reduce the size of the raw data set obtained from the apparatus. This may involve a reduction in pixel numbers by binning or cropping processes. Furthermore, the background in the EBSD image is removed by a known image processing technique, as is standard in EBSD, to separate the band information from the irrelevant background.

Figure 1:
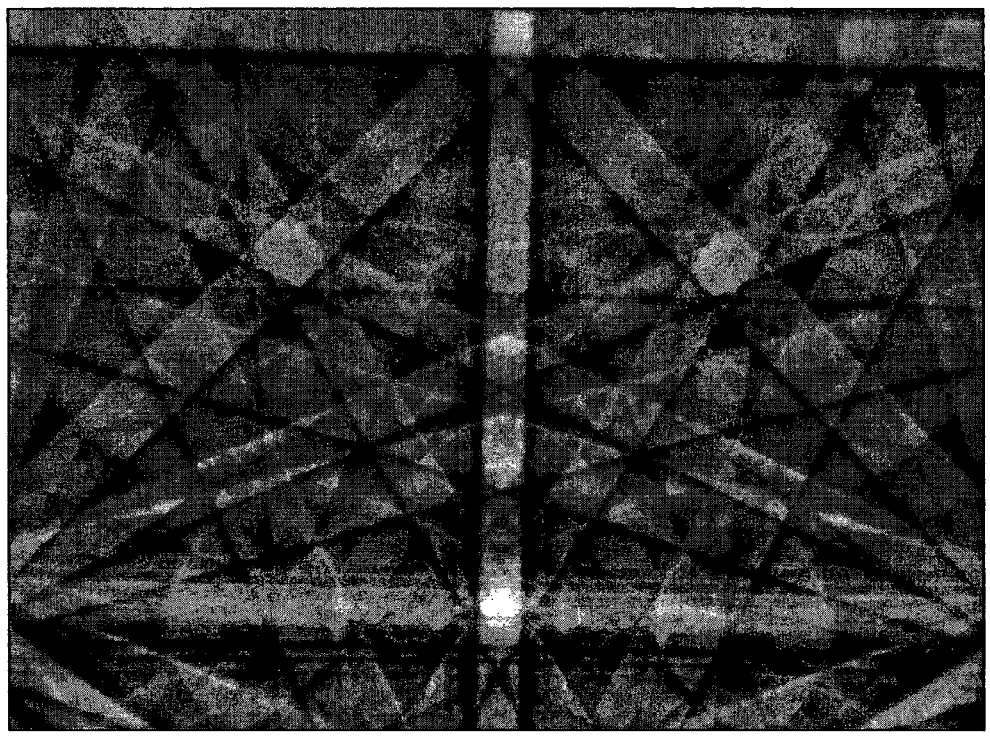
FIG. 1 is a representation of a typical electron diffraction image showing Kikuchi bands.
Figure 2:
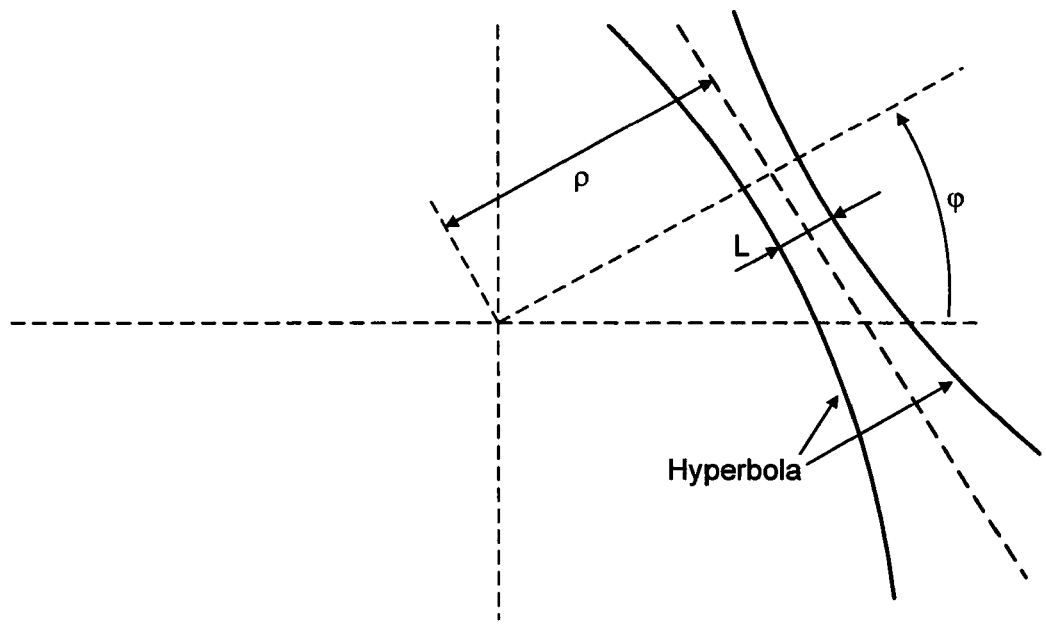
FIG. 2 shows parameters used to define the orientation of Kikuchi bands.
Figure 3:
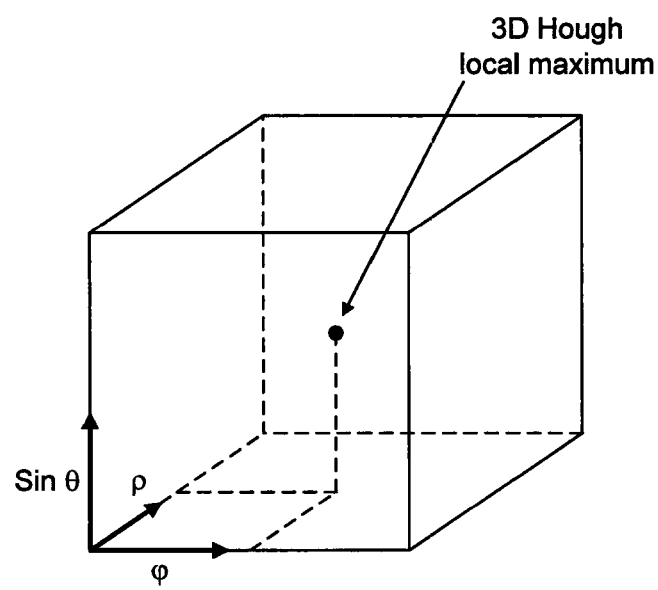
FIG. 3 shows a schematic diagram of the three-dimensional distance, angle and hyperbola space computed by the modified Hough transform and showing a local maximum corresponding to a Kikuchi band.

At step 120 a conventional two-dimensional ("2D") Hough transform is applied to this processed dataset to find straight line structure that is an approximation to the Kikuchi bands. If the original dataset is reduced (as is the case in step 110) the Hough transform can be calculated with a reduced calculation load at some expense to precision in locating band positions. The Hough transform converts the pattern into Hough space where a single spot represents a line in the original pattern with position and orientation given by the parameters rho and phi of FIG. 2.

Having converted the image data into "Hough space" at step 130 Kikuchi bands are detected by an algorithm for detecting local maxima in the Hough space. This algorithm starts with a digital filtering operation using a "butterfly filter" that takes account of the fact that the bands are broad and tends to emphasise the maximum and minima either side that correspond to a particular band. For each local maximum, the associated local minima are identified, being located on either "side" of the maximum, in the rho direction. Between each minimum and the maximum exists a position of maximum change in Hough value in the rho direction, and the mean of these two positions provides an initial estimate of band position in the Kikuchi pattern.

At step 140, the detected Kikuchi bands data are used in a conventional "indexing" step using known processes. This indexing makes a determination of the candidate phase that is present in the sample (at the point where the electron backscatter diffraction pattern was obtained) and identifies the detected bands crystallographically. In practice this step compares the inter-planar angles for subsets of bands, against those deduced from each crystallographic phase in a database of phases to find the phase that gives the most probable indexing for the bands. It is likely that some of the detected bands produce inter-planar angles that are not close to the actual ones for the best phase, but the bands that contribute to likely interplanar angles can now be identified with particular crystal planes and these bands can thus be "indexed". Typical numbers are 6 to 12 Kikuchi bands but the process may employ much larger number of bands in principle.

At step 150 a simulation is performed in which the Bragg angle is calculated for the indexed planes and selected phase using the known crystallographic data, and used together with the theory of Kikuchi pattern formation to simulate the edges of an individual band, given its approximate position and orientation as provided by the initial estimate step 130. Thus, the simulation calculates the two lines corresponding to Bragg reflection off the planes corresponding to this index for the candidate material at the optimum rotation.

At step 160, with the known and fixed Bragg angle for a specified individual band, and the initial estimate of the band orientation, the simulated edges are compared with the original high resolution Kikuchi pattern image. Then, at step 170, that particular band position, defined in polar coordinates (rho, phi), is modified iteratively in order to maximize the sum of slopes in image values across the simulated band edges, the slope being measured in the rho direction and defined positive if the change in image value decreases away from the band centre. In this way, the simulated Kikuchi bands are used to obtain an optimal fit between the crystallographic model and the experimental data. The Bragg angle affects the separation of the band edges and, at some computational cost, can also be included as a free parameter in the iterative refinement. It will be understood that the exact profile of a band is very complicated to predict and the position of the Bragg reflection does not always coincide with the position of maximum slope. In practice, this still allows the algorithm to find an optimum phi and rho. Increasing the Bragg angle increases the separation of the lines and this alters the locus of points used to calculate the sum of slopes. It does not alter the centre line of the band, which is determined by rho and phi, but adds a degree of freedom to the fit at the expense of additional computation time.

At step 180, the simulation (initial and iterative refinement) described in steps 150, 160 and 170 is applied to further bands but is typically only applied to those bands that are successfully indexed in step 140.

Each band at this stage has a known Bragg angle and iteratively refined rho and phi parameters as calculated by simulation and comparison with the EBSD image data.

At step 190, the iteratively matched band positions are then translated to their interpreted 3D plane normals, through the projection parameters (pattern centre and detector distance for the apparatus).

In a further step 200, the crystal orientation is determined as the rotation that best rotates the set of refined 3D plane normals into coincidence with the corresponding 3D lattice plane normals determined from the indexed bands. The degree of coincidence is expressed as "MAD", and is calculated as the mean angular deviation between corresponding 3D vectors after rotation.

In a further optional step 210, the crystal orientation calculated in the previous step is used to produce a Kikuchi pattern, which is presented to the user overlaid on top of the experimental data as a visual representation of the work performed. This step is not used when the method is used for unsupervised automatic indexing and refinement for a series of patterns.

There are a number of variable parameters that can be optimised for a particular specimen, microscope or desired precision. For example, a compromise exists between how much the data set is reduced in size (step 110) and the resultant precision, as a smaller data set lowers the computational expense of the Hough transform, but also increases error in the initial model parameters.

Further, because of the limited precision in the first identification of the bands (up to step 130) there may be a number of solutions in terms of candidate phases or alternative indexing for the same phase identified at step 140 that offer a similar quality of fit to the deduced interplanar angles. Therefore, if the parameters controlling the indexing cause multiple candidate solutions, the following steps 150 to 200 may be repeated for each candidate solution to find the one with the best refined mean angular deviation and this solution is then outputted as the identified phase and orientation. The method may be optimised further by running this refinement procedure only on phases selected automatically, or by the user, as higher precision may be required only for relevant phases and therefore the computation load can be reduced accordingly. In this case the remaining phases may be indexed by a procedure set out in steps 100 to 140.

Similarly, for a given phase, only a subset of Kikuchi bands may be used for refinement as their respective experimental data is sufficient for refinement. The basis for phase selection may be chemical filtering of a database or prior knowledge of which phases are contained in the sample. A basis for Kikuchi band selection may by a threshold that balances calculation load and number of bands, typically 8 to 12, or a filter that allows refinement of indexed bands only.

Each of these modified processes lends itself to automation and a reduction in computational load.

Figure 5:
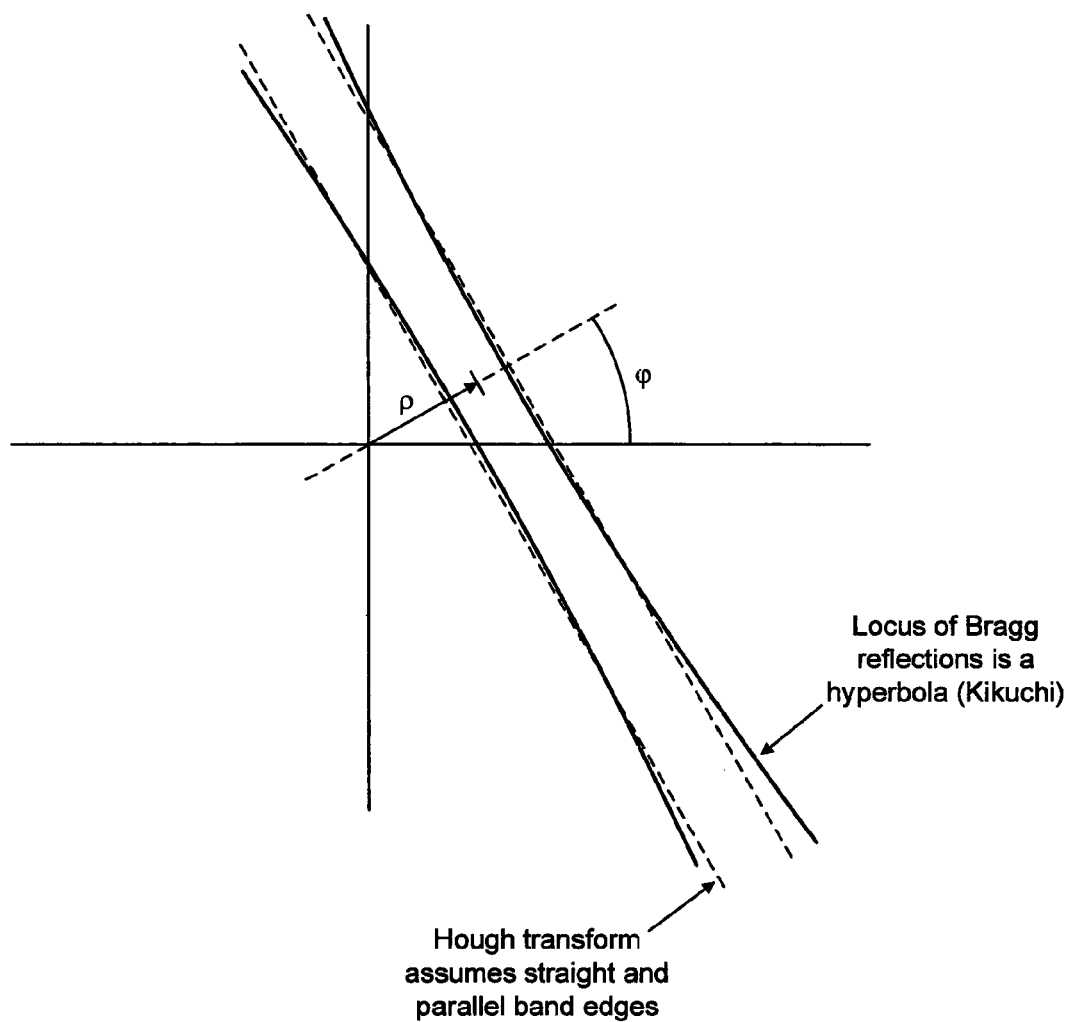
FIG. 5 shows Hough transformed lines and simulated Kikuchi hyperbolas.
Figure 6:
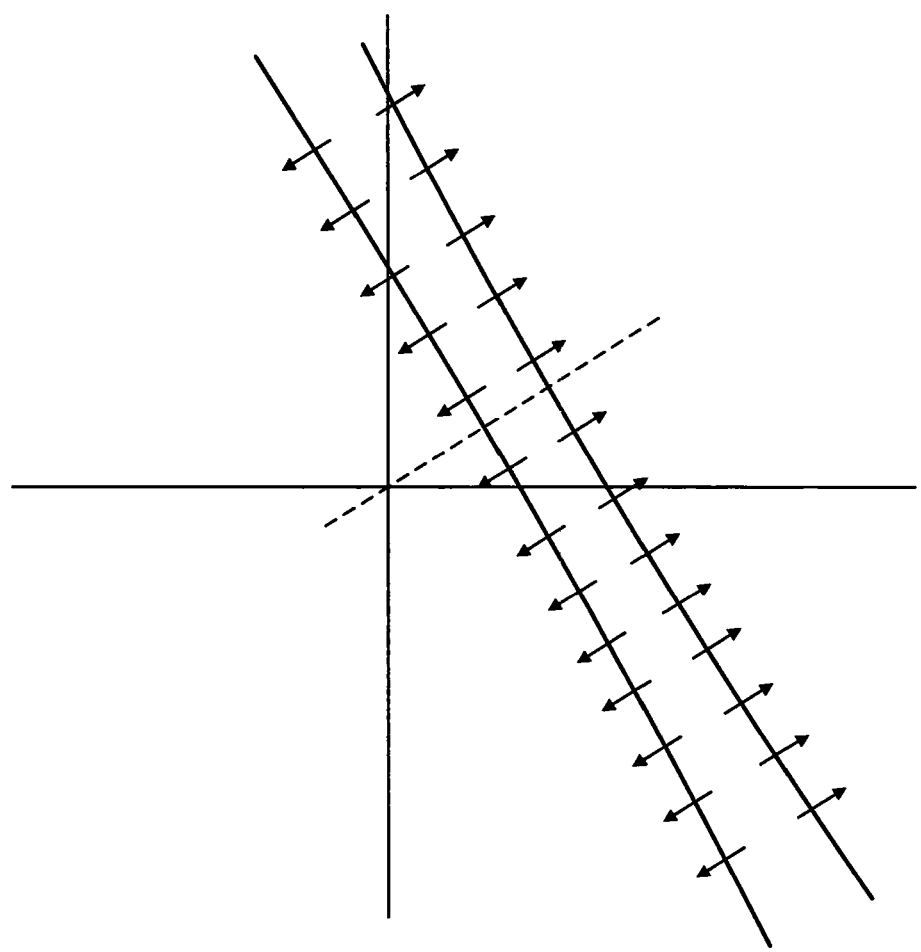
FIG. 6 illustrates sub-sampling along a band to reduce computational requirements.

FIG. 5 schematically illustrates the fit performed on only one Kikuchi band identified using the straight lines (dashed) corresponding to the approximate band edges consistent with the Hough transform result and then refined using the simulated Kikuchi bands, which include the crystallographic calculated hyperbolic profiles. Experimental data for a Kikuchi band used for refinement may be sub-sampled by skipping pixels along the band, and thus reducing the computation requirements further whilst maintaining adequate precision in crystallographic parameters. This is illustrated in FIG. 6 where lines represent the sub-set of pixel lines used for the refinement fit.

Figure 7:
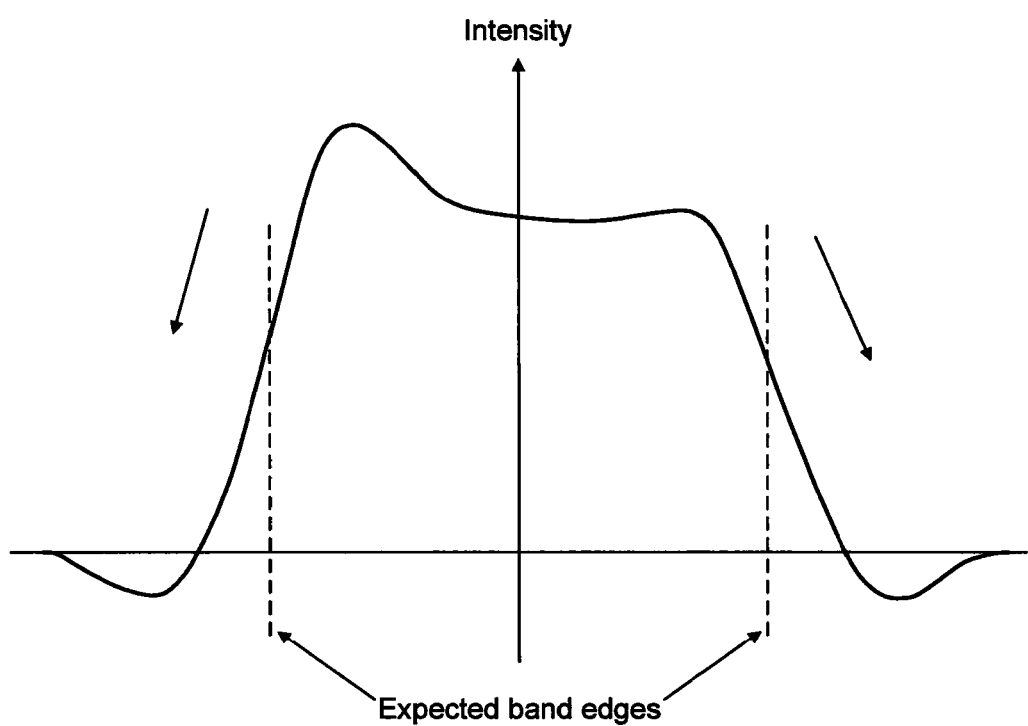
FIG. 7 shows a schematic section through a Kikuchi band in the rho direction.

As illustrated in FIG. 7, deficit and excess lines are expected in Kikuchi patterns and the corresponding up-down gradients across the band edges defined by the Bragg reflection condition can be checked to confirm that the band intensity conforms to the expected profile where, in the rho direction, the intensity or image value decreases away from the band centre at each edge. If this is not the case, the band is excluded from refinement and subsequent calculation of the orientation matrix and the MAD.

Parameters used for performing the fit may be selected according to specific needs of the user. If the Bragg angle has been included in the refinement the differences between expected and optimum Bragg angles for each band is influenced by a change in d-spacing and in principle could be used to deduce local strain in a map of crystallographic properties.

In the approach described, we have not attempted to refine a physical model of the specimen but rather have refined the parameters of each diffraction band, independently of any other. These parameters are typically just rho and phi, but they could also include the Bragg angle and are optimised to maximise a measure of fit to the band edges in terms of the sum of slopes of image values in the rho direction at multiple positions along these band edges. It will be appreciated that the same measure of fit could be used to adjust an initial solution for the physical model for a candidate phase to iteratively optimise the orientation and even the d-spacings for that phase. In this alternative approach, the starting point is the same candidate phase and set of indexed Kikuchi bands that define a candidate solution together with a first estimate of crystal orientation and optionally d-spacings. For each indexed Kikuchi band, the band edge positions are predicted from the physical model and the sum of slopes of image values is calculated at multiple points along the band edge as in the first approach. The sum or product of sums for all the indexed bands then becomes the measure that is maximised by iterative modification of the crystal orientation and optionally d-spacings and the maximised value of the measure for the candidate solution is used to choose between alternative candidate solutions. It may be preferable to use the average slope over the positions used for a band, rather than the sum of slopes, and maximise the average of average slopes for all the bands to normalise the measure in case alternative candidate solutions require iteration on different sets of indexed bands.

These methods improve the accuracy of band detection in comparison with known approaches and are achievable in real time applications. The methods use the primary band detection as their foundation, and then apply an iterative secondary band detection to improve upon the accuracy of the primary band detection.

This accurate determination of band positions enables the calculation of a more accurate orientation matrix and thus improves general EBSD analysis, such as the ability to distinguish between two phases with a very close crystal structure; or in characterizing low angle boundaries. In addition, this refinement will deliver an accurate solution when the primary band detection is impaired by the presence of excess and deficit lines.

The mean angular deviation (MAD) is a measure of the fit between the Kikuchi bands in the measured pattern and the solution. It can be used as figure of merit for the accuracy of band detection and therefore also for phase identification. Many applications of EBSD consider misorientation and the reliability of detection of small changes in grain orientation is improved by greater accuracy and precision in measuring crystal orientation.

Figure 8:
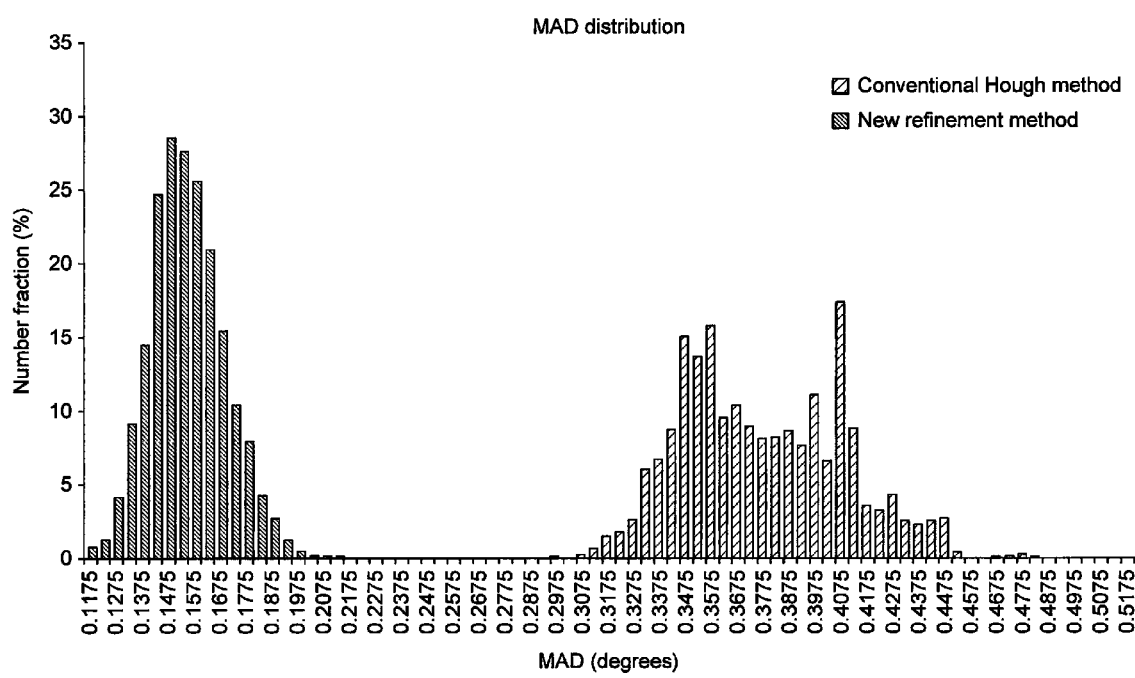
FIG. 8 shows a plot of MAD data for a single crystal.
Figure 9:
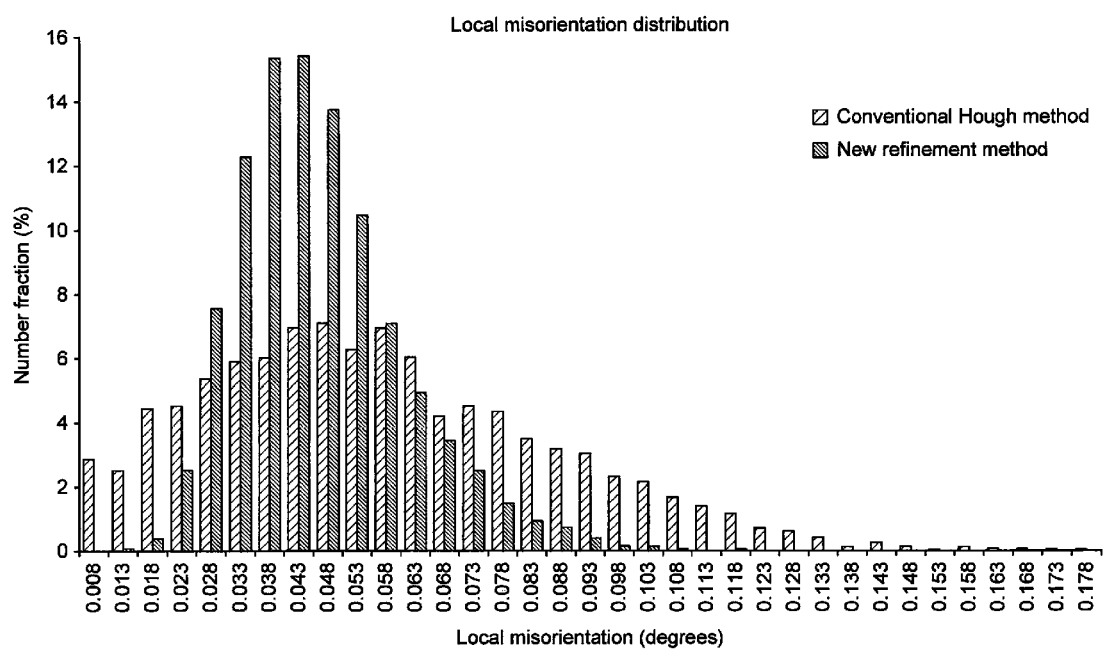
FIG. 9 shows a similar plot for misorientation data.

The benefits of the new approach presented herein can be seen in FIGS. 8 and 9. In this case a single crystal of silicon is used to characterise orientation precision; this removes complications resulting from the sample and simplifies analysis of different band detection and calibration methods. With a single crystal, the orientation should be constant throughout the field of view so differences in orientation from point to point are due to variability in the measurements. The same set of electron backscatter diffraction patterns from a single map are been processed using both the conventional Hough-based method and the new refinement method. FIG. 8 is a plot of MAD distribution and it can be seen clearly that the new method provides average mean angular distributions of around 0.15 degrees compared with generally more than 0.30 degrees for the prior method. FIG. 9 is a plot of local misorientation distribution. The local misorientation is a calculation of the average misorientation between each pixel and its nearest neighbours. Again the new refinement approach outperforms the prior art method by providing a much narrower distribution of misorientation values. These improvements indicate a more accurate fit between the pattern in the image and solution (MAD) which should yield benefits in ability to distinguish between phases and misorientation precision.

The invention claimed is:

1. A method for analysing electron backscatter diffraction data generated from a sample material, comprising:
   a) obtaining an image data set representative of an image of electron backscatter diffraction bands from the sample material;
   b) generating a set of estimated first diffraction parameters defining individual electron backscatter diffraction bands in the image data set;
   c) selecting a candidate phase and a set of plane indices consistent with a set of calculated plane normals for at least a subset of the defined diffraction bands;
   d) simulating identified diffraction bands for the candidate phase according to the Bragg angle for each indexed band and second diffraction parameters;
   e) adjusting, so as to refine, the second diffraction parameters for each of the simulated identified bands so as to maximize the sum of the slopes in the image values across the simulated band edges to fit each of the simulated bands to the corresponding identified bands in the image data; and,
   f) using the refined second diffraction parameters for the identified bands to calculate a fitted orientation for the candidate phase together with a corresponding fitting parameter defining the quality of fit,
   wherein the first and second diffraction parameters are rho and phi angles for the band centers of the simulated identified bands, each of which is modulated independently during the said adjusting of the second diffraction parameters in a fit to a single band.

2. A method according to claim 1, wherein the second diffraction parameters further comprise a Bragg angle that is modulated independently during the said adjusting of a fit to a single band.

3. A method according to claim 1, wherein the second diffraction parameters are modified iteratively in order to maximise the sum of slopes in image data values across the simulated band edges, the slope being measured in the rho direction and defined positive if the change in image value decreases away from the band centre.

4. A method according to claim 1, wherein the fitting parameter is a maximum angular deviation between the simulated and actual planes for the candidate phase.

5. A method according to claim 1, wherein the second diffraction parameters define the crystal orientation.

6. A method according to claim 1, wherein the second diffraction parameters define the crystal orientation and set of d-spacings.

7. A method according to claim 5, wherein the second diffraction parameters are modified iteratively in accordance with a correlation measure representing the correlation between chosen bands in an image data set and simulated bands in a simulated image.

8. A method according to claim 7, wherein the second diffraction parameters are modified iteratively in accordance with a correlation measure represented by a mathematical combination of slopes in image data values across the simulated band edges, the slope being measured in the rho direction and defined positive if the change in image value decreases away from the band centre.

9. A method according to claim 7, wherein the fitting parameter in step (f) is based upon the correlation measure.

10. A method according to claim 1, wherein, prior to step (a) the image data set is produced by processing an initial image data set so as to reduce the size of the image data set in comparison with the initial image data set.

11. A method according to claim 1, wherein step (b) comprises:
   (i) applying a Hough transform to the image data set forming transformed data in Hough space, and
   (ii) detecting Kikuchi bands in the Hough space.

12. A method according to claim 11, wherein step (c) comprises interpreting the detected Kikuchi bands to determine plane normals and comparing these with crystallographic data so as to index at least a subset of the bands.

13. A method according to claim 1, wherein in step (d) the number of bands simulated is smaller than the number of bands present within the image data set.

14. A method according to claim 1, wherein the number of bands simulated is equal to the number of bands for which estimated diffraction parameters are generated in step (b).

15. A method according to claim 1, further comprising, selecting a plurality of candidate solutions, each having a phase and set of indices for each band in accordance with step (c), performing steps (d), (e) and (f) for each candidate solution and selecting a resultant phase and associated fitted orientation based upon the fitting parameter for each solution.

16. A method according to claim 1, wherein the effect of the adjustment in step (e) is calculated at a number of separated locations along the bands.

17. A method according to claim 1, further comprising producing an image of the bands of the image data set overlaid with the simulated bands.

18. A method according to claim 1, wherein the method is repeated for a number of scan points on the sample so as to produce a map of crystallographic properties.

* * * * *